US007702526B2

(12) United States Patent
Alemi et al.

(10) Patent No.: US 7,702,526 B2
(45) Date of Patent: Apr. 20, 2010

(54) ASSESSMENT OF EPISODES OF ILLNESS

(75) Inventors: Farrokh Alemi, McLean, VA (US); Valentin Prudius, Oak Hill, VA (US)

(73) Assignee: George Mason Intellectual Properties, Inc., Fairfax, VA (US)

( * ) Notice: Subject to any disclaimer, the term of this patent is extended or adjusted under 35 U.S.C. 154(b) by 1660 days.

(21) Appl. No.: 10/054,706

(22) Filed: Jan. 24, 2002

(65) Prior Publication Data

US 2003/0139947 A1    Jul. 24, 2003

(51) Int. Cl.
*G06Q 50/00* (2006.01)
(52) U.S. Cl. .................................. 705/3; 705/2; 705/4
(58) Field of Classification Search ................ 705/2, 705/3, 4; 600/300, 393, 529
See application file for complete search history.

(56) References Cited

U.S. PATENT DOCUMENTS

| | | | | | |
|---|---|---|---|---|---|
| 5,508,912 | A | * | 4/1996 | Schneiderman | 705/3 |
| 5,557,514 | A | * | 9/1996 | Seare et al. | 705/2 |
| 5,706,441 | A | * | 1/1998 | Lockwood | 705/3 |
| 5,819,228 | A | * | 10/1998 | Spiro | 705/2 |
| 6,061,657 | A | * | 5/2000 | Whiting-O'Keefe | 705/2 |
| 6,151,581 | A | * | 11/2000 | Kraftson et al. | 705/3 |
| 2002/0019747 | A1 | * | 2/2002 | Ware et al. | 705/2 |
| 2002/0103622 | A1 | * | 8/2002 | Burge | 702/183 |
| 2003/0036683 | A1 | * | 2/2003 | Kehr et al. | 600/300 |
| 2003/0055680 | A1 | * | 3/2003 | Skeba | 705/2 |
| 2003/0125632 | A1 | * | 7/2003 | Takizawa | 600/509 |
| 2003/0195838 | A1 | * | 10/2003 | Henley | 705/37 |
| 2005/0125257 | A1 | * | 6/2005 | Ziegele et al. | 705/3 |

OTHER PUBLICATIONS

"Managed Care, Capitation Slowly Take Root in Home Care Industry." Medicine & Health, v 51, n. 11, Mar. 17, 1997.*

* cited by examiner

*Primary Examiner*—James A Kramer
*Assistant Examiner*—Martin A Gottschalk
(74) *Attorney, Agent, or Firm*—David G. Grossman; David Yee

(57) ABSTRACT

An episode classification system including a multitude of diagnosis records. Each of the diagnosis records includes diagnoses information, time of diagnoses information, and patient information. A patient grouper generates at least one patient group by grouping patient records having similar patient information. A diagnosis grouper generates at least one diagnosis group from a patient group by grouping patient records from a patient group that have similar diagnosis information. An episode analyzer includes a probability analyzer, an episode grouper, and a severity analyzer. The probability analyzer performs probability calculations capable of generating a probability value using at least two of the diagnosis records as input entries. The probability value represents the probability that the input entries belong to a single episode. The episode grouper groups diagnosis records determined to belong to a single episode. The severity analyzer performs episode severity calculations capable of generating an episode severity value.

4 Claims, 6 Drawing Sheets

ASSESSMENT OF EPISODES OF ILLNESS

BACKGROUND OF THE INVENTION

The present invention relates to field of health management systems. More specifically, the present invention provides for identifying episodes of care and measuring the severity of an episode.

Measures of episodes of care may be used to set capitation rates or to profile clinicians' performance. Numerous approaches to measuring episodes of care exist. Examples include Prospective Risk Adjustment, Ambulatory Visit Groups, Disease Staging, Products of Ambulatory Care, Ambulatory Diagnosis Groups and Ambulatory Care Groups. In addition to broad approaches to measurement of episodes of illness, many have developed disease specific episodes of care.

Three problems exist with the current approaches to measuring episodes of care. First, no current approach provides a mathematical model for measuring episodes of care. Most existing approaches to measuring episodes of care do not describe the internal procedures used for measuring severity or identifying episodes of care. Some commercial approaches seem to consider such information as business secrets that and do not disclosed internal procedures. Even when they do describe the internal mechanism of their approach, all appear to rely on heuristics that make clinical sense but do not provide a mathematical theory for the relation between the variables used in constructing episodes of care. Thus, researchers face a black box—the content of which they know little about or may be based on heuristics that they cannot easily modify and reapply. In the absence of a theory, it is difficult to learn from one study how better measures can be constructed. Each study and each approach exists on its own merits and fails to contribute to the other. Researchers then tend to compete on claims of accuracy rather than to build on each other's work. As a result, while many approaches exist, there is little cumulative progress in the field. The ability of one investigator to build on another person's approach has been limited. What is needed is a mathematical theory that allows for the accumulation of information to improve our understanding of how severity of episodes of care should be measured. Then, future researchers may change be able to modify or change theories to arrive at predictions that are more accurate. Theories may be modified and knowledge accumulated as new insights are found.

Second, current approaches do not allow for identifying episodes of care without first classifying diagnoses into clusters of diseases. All existing approaches are built on the concept of classifying possible diagnoses into a few clusters and then findings rules for creating episodes for these clusters. Schneeweiss and colleagues in an article entitles "Diagnostic clusters: A new tool for analyzing the content of ambulatory medical records," in Medical Care 1983, XXI (1): 105-122, reported that 92 diagnosis clusters make up 86 percent of all ambulatory visits. Others have expanded this set to 125, with varying levels of severity and different periods of time, during which the diagnoses in the cluster belongs to the same episode. What is needed is an approach that does not attempt to reduce the large set of possible diagnoses into a smaller set of clusters. Reductionist approaches, by definition, give up important nuances in order to have a manageable set of diagnoses. For example, infections often follow wounds and therefore may be considered part of the same episode. But an otitis media, even though an infection of the ear, could not possibly be part of an episode of trauma to the leg. Defining all infections as one cluster of diagnoses forces investigators to ignore important differences that might exist between types of infections. It may be important that operations are defined on individual diagnoses without need to pre-set diagnoses into broad clusters. Sometimes classification of diseases into clusters is based on the etiology of the disease, leading to possible counter intuitive classifications. An episode of trauma may include a fracture to the knee as well as a fracture of the leg, even though the knee fracture and leg fracture are different problems. Similarly, congestive heart failure may be part of an episode of myocardial infarction even though one involves the heart the other the lung. Two very dissimilar diagnoses may be part of the same episode, even though these diagnoses do not describe the same illness.

Third, many current approaches create homogenous resource use episodes. Not all follow-up visits are part of the same episode even though they may all be short visits and therefore have similar resource use. The nature of the diagnosis, not the intensity of visits should be the basis of classifying visits into episodes. For example, follow-up visit for myocardial infarction is part of an MI episode and a follow-up visit for trauma is part of trauma episode. Intensity-based measures may not be used for evaluating whether the numbers of visits are appropriate. In essence, they are fee schedules, except that these fee schedules are based on groups of visits or diagnoses and not single visit diagnosis. What is also needed is a relation-based episode classification system that remedies this important shortcoming. A elation-based episode classification system may be used to judge appropriateness of number of visits.

Efficient healthcare management requires accurately tracking the diagnosis and care of illness beyond what is currently in use. What is needed is a relation-based episode classification system that allows for the accumulation of information to improve the understanding of how severity of episodes of care may be measured without reducing the large set of possible diagnoses into a smaller set of clusters.

BRIEF SUMMARY OF THE INVENTION

One advantage of the present invention is that it may produce measures of illness from information collected by healthcare related services such as clinics, hospitals, private providers and insurance.

Another advantage of this invention is that it may allow for the accumulation of information to improve the understanding of how severity of episodes of care may be measured without reducing the large set of possible diagnoses into a smaller set of clusters.

Another advantage of this invention is that it may be implemented on any administrative or encounter database, which has information on date of visit and diagnosis.

A further advantage of this invention is that it may provide for outcome and efficiency analysis relating to common episodes of care for illnesses.

Yet a further advantage of this invention is may be used to construct episodes of care for specific diseases.

To achieve the foregoing and other advantages, in accordance with all of the invention as embodied and broadly described herein, an episode classification system including a multitude of diagnosis records, each of the diagnosis records including diagnoses information, time of diagnoses information, and patient information. A patient grouper may generate at least one patient group by grouping patient records having similar patient information. A diagnosis grouper may generate at least one diagnosis group from a patient group by grouping patient records from a patient group that have similar diagnosis information. An episode analyzer may include a probability analyzer, an episode grouper, and a severity analyzer. The probability analyzer may perform probability calculations capable of generating a probability value using at least two of the diagnosis records as input entries. The probability value may represent the probability that the input entries belong to a single episode. The episode grouper may group diagnosis records determined to belong to a single episode. The severity analyzer may perform episode severity calculations capable of generating an episode severity value.

In yet a further aspect of the invention, a probability calculation may operate on a pair of diagnosis records, and may be a function of a similarity value and a time between diagnosis value. The similarity value may represent the similarity between the pair of diagnostic records; and the time between diagnosis value may represent the time between the pair of diagnostic records.

In yet a further aspect of the invention, the probability calculation may also include a probability numerator divided by a probability denominator The probability numerator may be set to the similarity value times a first constant, and the probability denominator may be set to the quantity of a second constant times the time between diagnosis value plus one.

In yet a further aspect of the invention, a classification of diagnoses into episodes. Diagnosis information is preferably classified into at least one episode using standardized scores. The step of classifying each of the diagnosis information into at least one episode may include several steps. A first step may include flagging each of the diagnosis information in the patient group for analysis. Until all diagnosis information in the patient group is analyzed, a series of steps may be performed. Two of the diagnosis information(s) in the patient group flagged for analysis, which preferably has the maximum standardized scores not exceeding a preset cutoff, may be combined into an episode record. New diagnosis information representing the diagnosis information in the episode record may be created. A new standardized score for the new diagnosis information may then be calculated by averaging the standardized score associated with each of the diagnosis information in the episode record. The diagnosis information in the episode record may be de-flagged, indicating that it should not be used for further analysis. A determination may be made as to whether any diagnosis information still needs to be processed. If the determination is positive, then the process may repeat.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated in and form a part of the specification, illustrate an embodiment of the present invention and, together with the description, serve to explain the principles of the invention.

DETAILED DESCRIPTION OF THE INVENTION

Figure 1:
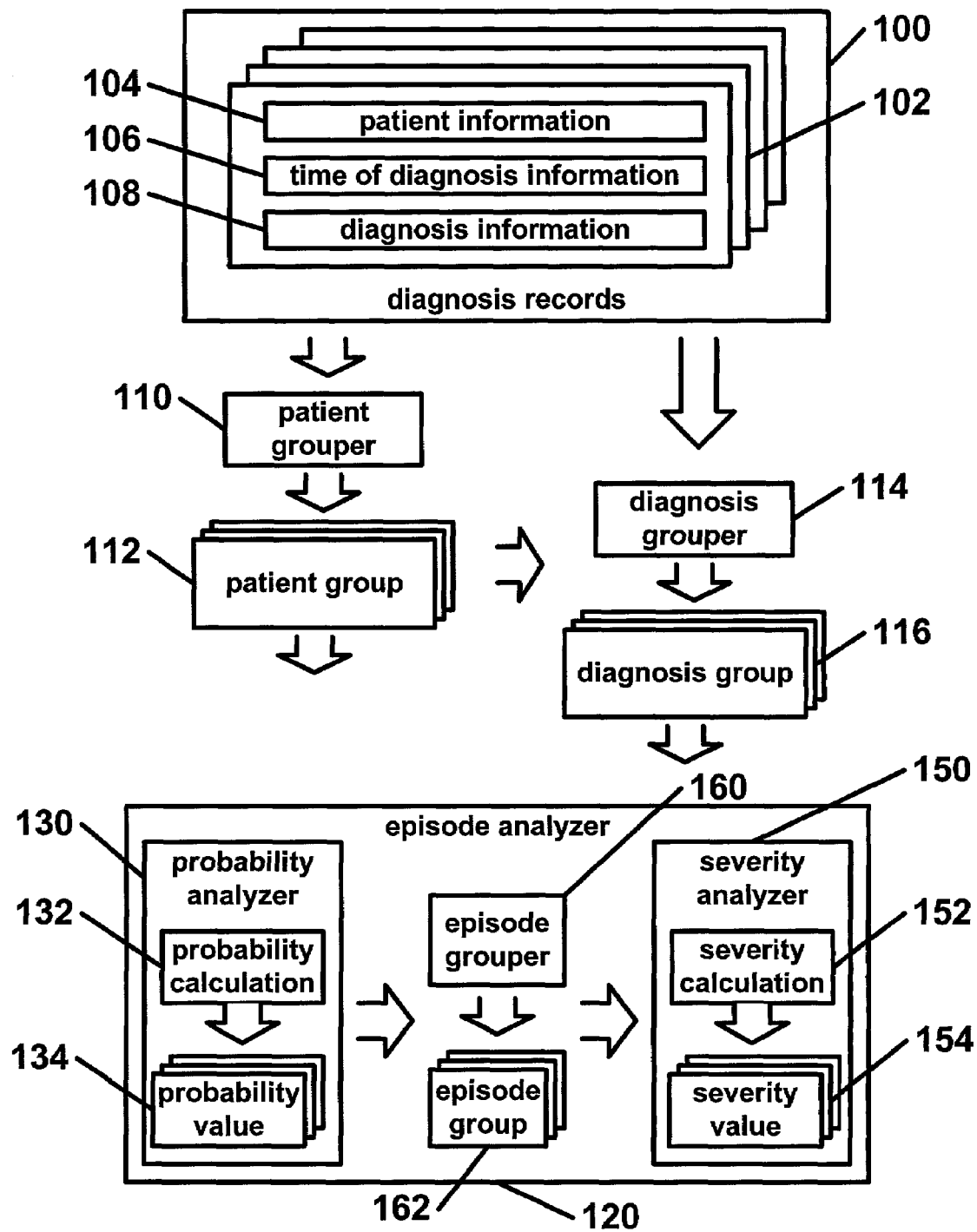
FIG. 1 shows an embodiment of an episode classification system as per the present invention.

The present invention is a relation-based episode classification system that allows for the accumulation of information to improve the understanding of how severity of episodes of care may be measured without reducing the large set of possible diagnoses into a smaller set of clusters.

An episode of care may be defined as a group of diagnoses on the same patient that describes the course of a given illness. Note that this definition does not depend on the nature of services delivered, the doctor delivering services, or the site of services. Nor, contrary to other definitions, does this definition assume that services are temporally contiguous. Thus, this definition allows for episodes to be overlapping; for example, a patient may have an acute exacerbation of their chronic diabetes and experience an episode of upper respiratory infection.

Episodes may be characterized by an anchor diagnosis. An anchor diagnosis is preferably the diagnosis that gives its name to the episode. Episodes generally have starting points (sometimes referred to as trigger diagnosis) and stopping points that may be different from the anchor diagnosis. Episodes may be characterized by a rate of progression, a peak severity during the course of episode, and morbidity and mortality outcomes. One episode, for example, may have a rapid onset, progress to a very serious condition, and then lead to death. Another episode may have a slow onset and never become serious.

Defining an episode may begin with selecting diagnoses that are part of the same episode. Imagine that a patient has had a series of diagnosis D1, D2, ... Dm at times T1, T2, through Tm. Whether two diagnoses are part of the same episode may depend on the nature of the two diagnoses and the time between them. Two diagnoses that are similar or related in nature should be part of the same episode unless they occur at significantly different times. If we define $P_{ia}$ as the probability that the diagnosis "i" and diagnosis "a" belong to the same episode, then the theory suggests that:

$$P_{ia}=\text{function}\{T_{ia},S_{ia}\}$$

Where the similarity between the diagnosis "i" and diagnosis "a" is $S_{ia}$; and number of days between diagnosis "i" and diagnosis "a" is $T_{ia}$ and calculated as:

$$T_{ia}=T_a-T_i \; T_{ia}>0$$

Note that the probability of being part of the same episode, $P_{ia}$, should be directly related to similarity of two diagnoses $S_{ia}$, and inversely related to $T_{ia}$, the time between the two diagnoses. A specific mathematical function that preserves these two relationships is:

$$P_{ia}=\alpha S_{ia}/(1+\beta T_{ia})$$

In the above equation, $\alpha$ and $\beta$ are preferably constants.

When a patient receives several diagnoses, then the probability that any two of the diagnoses may belong to an episode may be calculated using the above formula. Later, these pairwise probabilities of belonging to the same episode may be used to classify diagnosis into groups—using one of many widely available classification methods, including one disclosed herein.

Diagnoses may differ in terms of their severity. The severity of a diagnosis "i" may be represented as $Sev_i$. The overall severity of an episode may be calculated using the following multiplicative mathematical formula:

Overall severity of episode=$1-\pi_i(1-Sev_i)$

There are many different mathematical formulas for aggregating severity of individual diagnosis to severity of an episode. A common approach is to add or average the severity scores for each diagnosis. Adding scores may not be appropriate, as episodes with few severe diagnoses would be scored lower than episodes with many non-severe diagnoses. Averaging may also not be appropriate, as patients who have two diagnoses, one severe and the other not, may be rated lower than patients with just the severe diagnosis. Instead of adding or averaging the scores, a multiplicative model as above may be used. For example, if a patient has two diagnoses, one with a severity score 0.9 and another with a severity score 0.5, then the overall severity of the episode may be calculated as:

Overall severity for the patient=$1-(1-0.9)*(1-0.5)=$ 0.95

Compared to the adding or the averaging formula, the multiplicative formula has several advantages: The influence of severe diagnoses on the overall score may not be diluted by non-severe diagnoses and merely increasing the number of diagnoses may not necessarily result in high overall severity scores.

Referring to FIG. 1, an embodiment of an episode classification system as per the present invention including a multitude of diagnosis records 100 is shown. Each of the diagnosis records 100 may include diagnoses information 108, time of diagnoses information 106, and patient information 104. A patient grouper 110 may generate at least one patient group 112 by grouping patient records having similar patient information 104. The diagnosis grouper 114 preferably generate at least one diagnosis group 116 from a patient group 112 by grouping patient records from a patient group 112 that have similar diagnosis information. An episode analyzer 120 may include a probability analyzer 130, an episode grouper 160, and a severity analyzer 150. The probability analyzer 130 preferably performs probability calculation(s) 132 capable of generating probability value(s) 134 using at least two of the diagnosis records as input entries The probability value 134 may represent the probability that the input entries belong to a single episode. The episode grouper 160 may group diagnosis records determined to belong to a single episode. The severity analyzer 150 may perform episode severity calculations 152 capable of generating episode severity value(s).

Diagnosis records may include anchor diagnosis record(s), trigger diagnosis record(s), and stopping point diagnosis record(s).

The probability calculation 132 may operate on a pair of diagnosis records, and may be a function of a similarity value and a time between diagnosis value. The similarity value may represent the similarity between the pair of diagnostic records; and the time between diagnosis value may represent the time between the pair of diagnostic records.

The probability calculation 132 may also include a probability numerator divided by a probability denominator The probability numerator may be set to the similarity value times a first constant, and the probability denominator may be set to the quantity of a second constant times the time between diagnosis value plus one.

Figure 2:
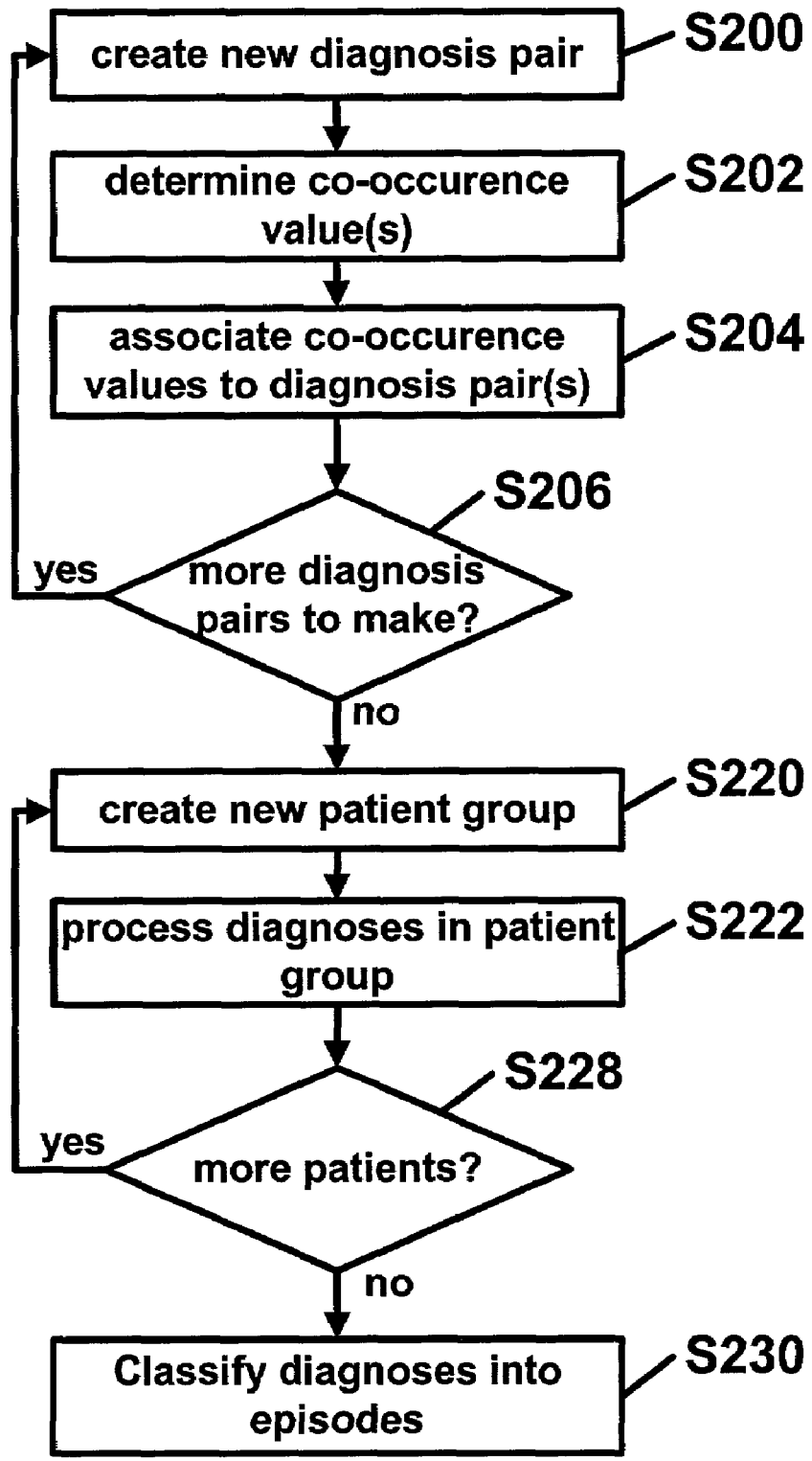
FIG. 2 is a flow diagram of an episode classification system as per an embodiment of the present invention.

FIG. 2 is a flow diagram of an aspect of an embodiment of the present invention showing a method for an episode classification system using a multitude of diagnosis records 100 including: diagnosis information 108; time of diagnoses information 106; and patient information 104. The method for episode classification using diagnosis records 100 may start with the step of creating at least one diagnosis pair (S200) from the diagnosis records 100. Each diagnosis pair may contain a unique combination of two diagnoses information 106.

For each diagnosis pair, a co-occurrence value may be determined (S202). The co-occurrence value may be the number of unique patients for whom the two diagnoses contained in each of the diagnosis pairs occurred within a co-occurrence window. The co-occurrence value may be associated with each diagnosis information contained in the diagnosis pair (S204). These steps may be repeated iteratively until there are no more unique diagnosis pairs to make (S206).

At least one patient group may be created at step S220. Each patient group may be generated by grouping the diagnosis records having similar patient information. For each patient group, the diagnoses should be processed (S222) until all of the diagnosis records for all of the patient have been completed (S228). The diagnoses may now be classified into episode(s) at step S230.

Figure 3:
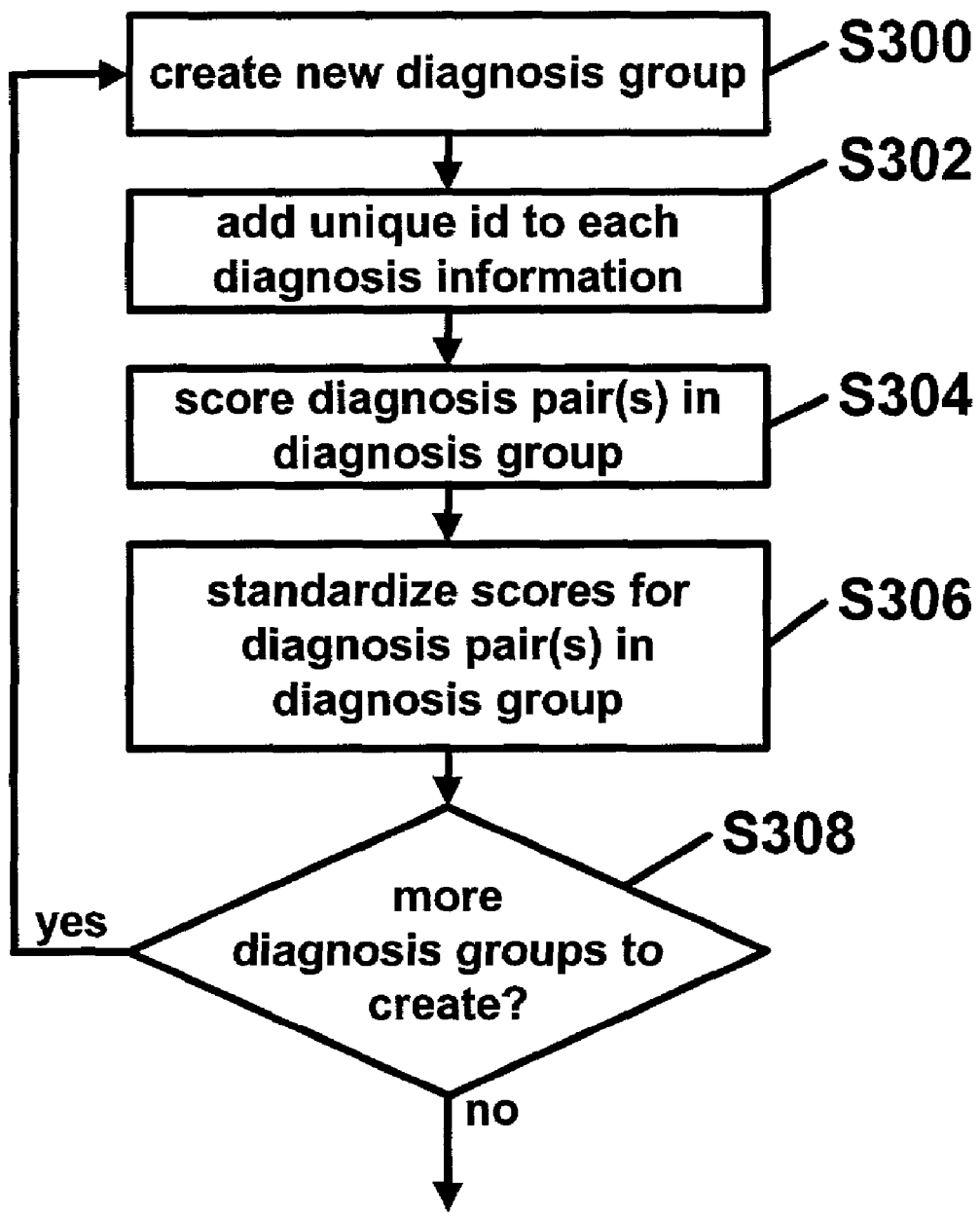
FIG. 3 is a flow diagram of an aspect of an embodiment of the present invention showing creation and processing of diagnosis groups.

FIG. 3 is a flow diagram of an aspect of an embodiment of the present invention showing an iterative process for creating and processing diagnosis groups (S222). A diagnosis group is preferably created at step S300. Diagnosis groups may be generated by grouping the diagnosis records 100 having similar diagnosis information 108. For each diagnosis group 116, a unique occurrence identifier may be iteratively added to the diagnosis information 108 at step S302 for each the diagnosis record 102. Next, diagnosis pair(s) in the diagnosis group may be scored at step S306. At step S308, a determination may be made if more diagnoses groups are needed. If the determination is positive, then the process may return to step S300. Step S308 preferably allows for the diagnosis grouping and scoring process to continue until diagnosis information has been processed.

Figure 4:
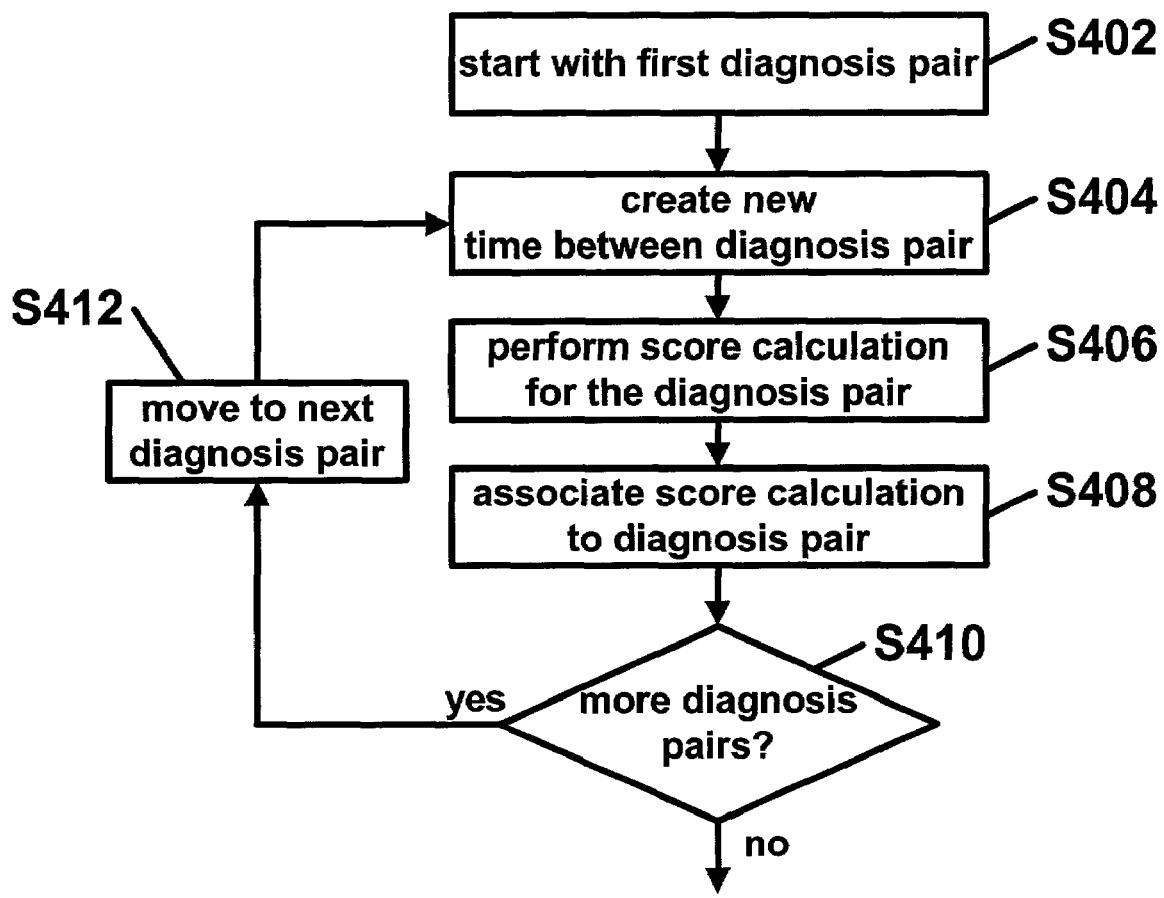
FIG. 4 is a flow diagram of an aspect of an embodiment of the present invention showing diagnosis pair scoring.

FIG. 4 is a flow diagram of an aspect of an embodiment of the present invention showing diagnosis pair scoring (S304). Starting with a first diagnosis pair (S402), a time between diagnosis pair from the diagnosis records in the diagnosis group may be created at step S404. Each of the time between diagnosis pairs may contain a unique combination of two diagnosis records 100.

A score calculation may be performed for the diagnosis pair (S406). For each time between diagnosis pair, a time between diagnosis pair value for each diagnosis pair may be set equal to the absolute value of the difference between the time of diagnoses information from each diagnosis record in the diagnosis group. A score numerator may be set equal to the co-occurrence value having the same combination of diagnosis information as the time between diagnosis pair value. A score for the diagnosis pair may then be calculated by dividing the score numerator by the time between diagnosis pair value.

The score may be associated to the diagnosis pair at step S408. A determination may be made at step S410. If the determination is positive, then the process may move to the next diagnosis pair at step S412 and continue again at step S404.

Figure 5:
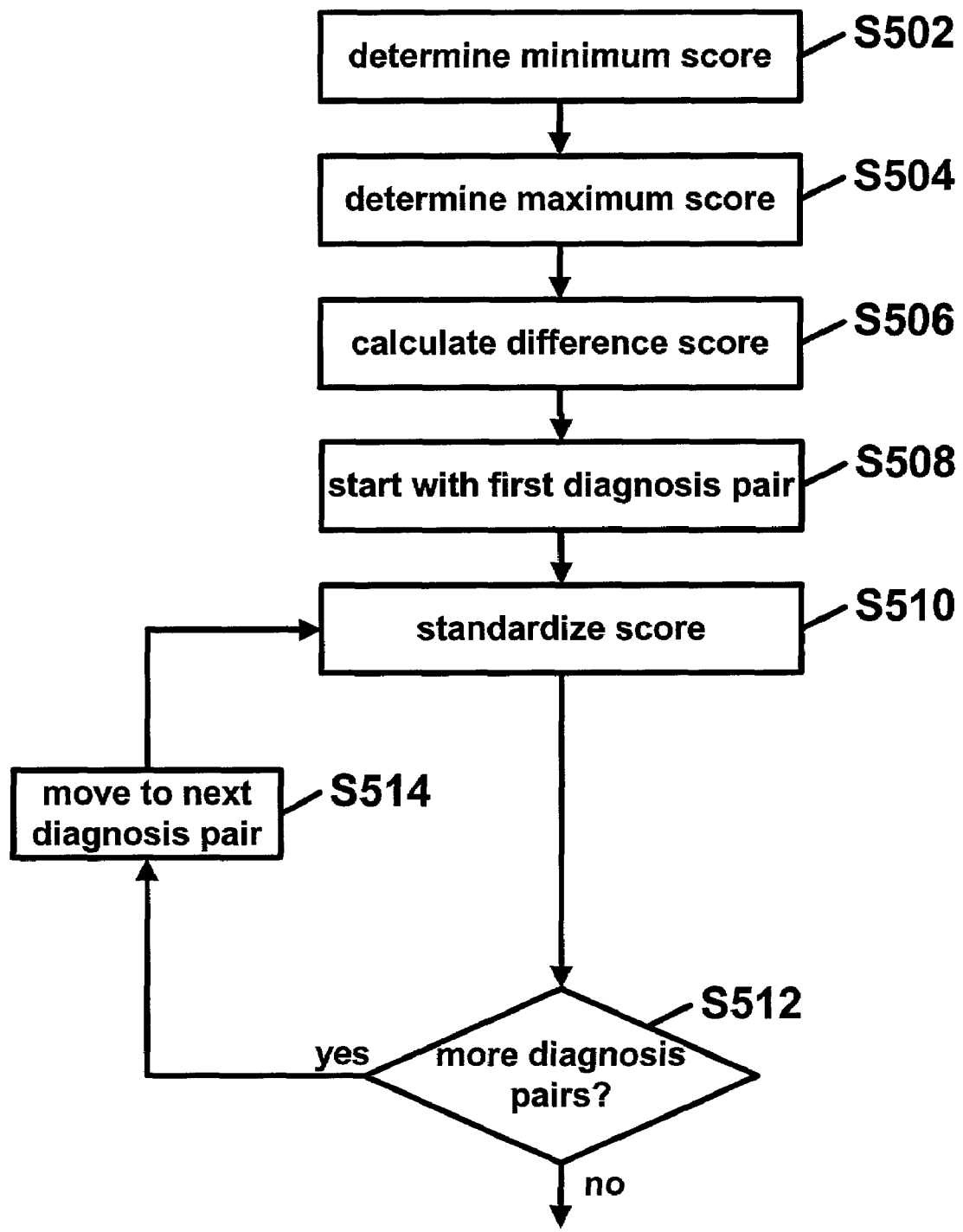
FIG. 5 is a flow diagram of an aspect of an embodiment of the present invention showing standardized scoring of diagnosis pairs.

FIG. 5 is a flow diagram of an aspect of an embodiment of the present invention showing standardized scoring of diagnosis pairs (S306). A minimum score value may be set to equal the minimum score from the set of scores associated with each of the diagnosis pairs in the patient group at step S502. A maximum score value may then be set to equal the maximum score from the set of scores associated with each of the diagnosis pairs in the patient group at step S504. At step S506, a difference score value may be set to equal the difference of the maximum score value and the minimum score value.

A series of steps may be performed for each of the diagnosis pair(s) to create a standardized score for each diagnosis pair. Starting with a first diagnosis pair, a standardized score may be calculated at step S510. A standardized score numerator value may be set equal to the minimum score minus the score associated to the time between diagnosis pair. A standardized score may be set equal to the standardized score numerator divided by the difference score value. The standardized score may be associated with the diagnosis pair. At step S512, a determination as to whether more diagnosis pairs need to have their scores standardized may be made. If the determination is positive, then the process may move to another diagnosis pair S514 and continue at step S510.

Figure 6:
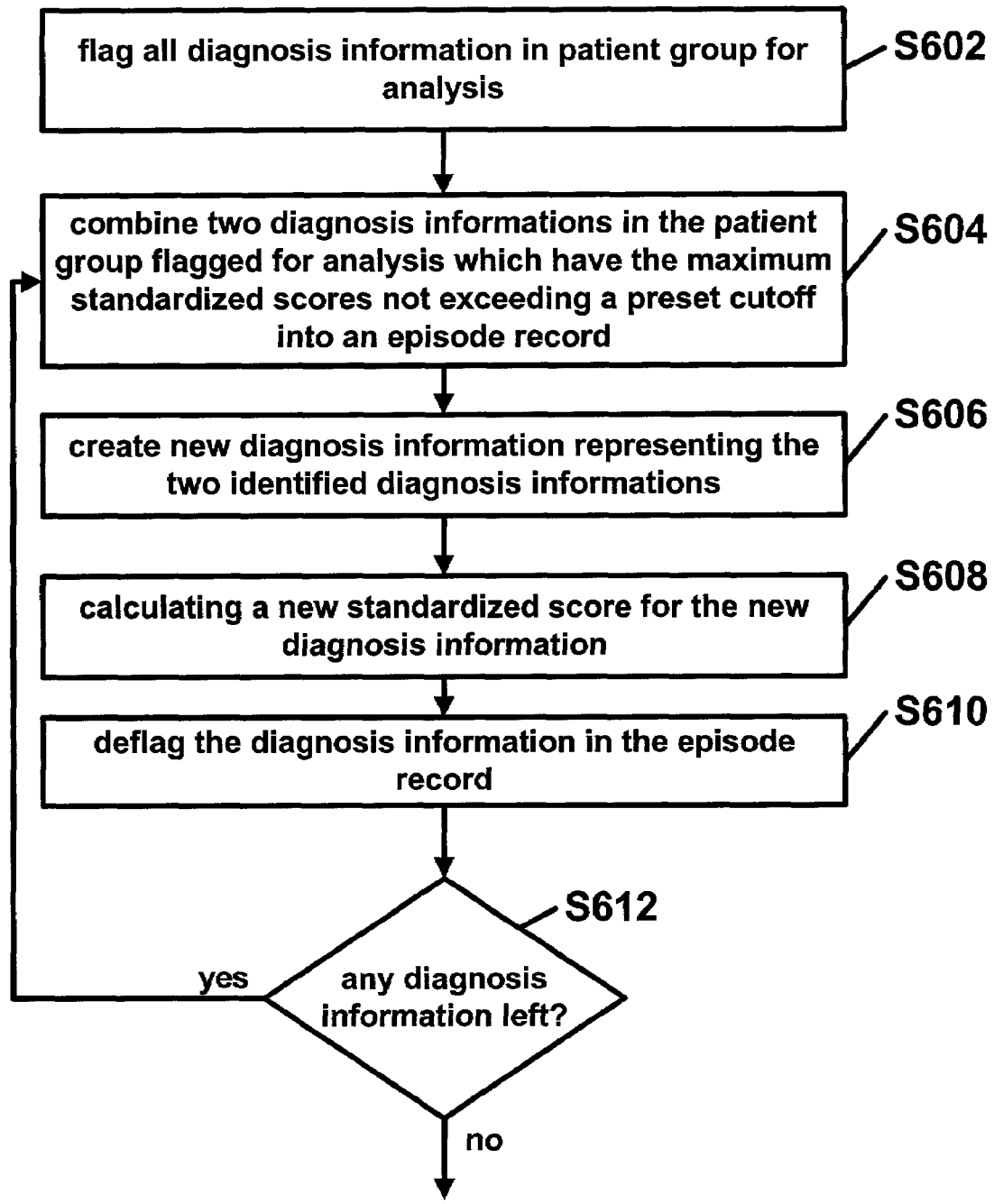
FIG. 6 is a flow diagram of an aspect of an embodiment of the present invention showing classification of diagnoses into episodes.

FIG. 6 is a flow diagram of an aspect of an embodiment of the present invention showing classification of diagnoses into episodes (S230). Each diagnosis information is preferably classified into at least one episode using standardized scores. The step of classifying each of the diagnosis information into at least one episode may include several more steps. A first step may include flagging each of the diagnosis information in the patient group for analysis at step S602.

Until all diagnosis information in the patient group is analyzed, a series of steps may be performed. Two of the diagnosis information(s) in the patient group flagged for analysis which preferably have the maximum standardized scores not exceeding a preset cutoff may be combined into an episode record at step S604. At step S606, new diagnosis information representing the diagnosis information in the episode record may be created. A new standardized score for the new diagnosis information may then be calculated at step S608 by averaging the standardized score associated with each of the diagnosis information in the episode record. The diagnosis information in the episode record may now be de-flagged at step S610, indicating that it should not be used for further analysis. At step S612, a determination may be made as to whether any diagnosis information still needs to be processed. If the determination is positive, then the process may continue at step S604.

An illustrative example using the present invention and measurement of parameters created from a measure for severity of episodes of illness for developmentally delayed children who were enrolled in the Medicaid program of one Southeastern State will now be described. Developmentally delayed children use health services extensively. To reduce computational difficulties and without loss of generality, 565 patients among the 3250 patients in a database were randomly sampled.

The data included both in-patient and outpatient Medicaid payments for the patient. The in-patient portion included both the health professionals billing and the institution's bills. On average, the State paid $9,296 per patient per year. The standard error of the cost was $2,238, reflecting large variation in cost of care across patients. Cost ranged from $29 (reflecting patients enrolled for portion of the year) to $884,967 per year.

Estimating the time between two diagnoses, $T_{ia}$, was determined directly from the database by taking the absolute value of the difference in dates of the two diagnoses. Estimating the similarity of the two diagnoses, $S_{ia}$, was more difficult. A surrogate measure of similarity of two diagnoses may be the number of times the two diagnoses co-occur within a specific time frame. An implicit assumption was made that complications and related problems tend to occur in clusters. One skilled in the art will recognize that assumptions and estimation techniques used in this example are example specific, and that the invention is not limited to using such assumptions and estimations.

A score proportional to the likelihood that two diagnoses belong to the same episode by the formula for an 'overall severity of episode' provided earlier was then calculated. This score was then used to classify diagnoses into episodes in such a manner that diagnoses within one episode were more similar than diagnoses in different episodes. Appendix A gives a detailed example of how diagnoses were classified. The mean number of episodes was 147 (standard error=320). Patients differed considerably in the number of episodes they had.

The severity of each diagnosis as the average amount paid for the diagnosis was then calculated. Severity and costs may not always be related, especially when patients die before expensive services may be delivered. But in this example database, no patient passed away. Therefore, cost may have been a reasonable surrogate measure of severity.

To test the accuracy of measures of episodes of care in this illustrative example, cost of care on severity of the episode, number of episodes and interaction between number of episodes and severity of episodes was regressed. Cost of care was measured by the amount the State paid for each encounter. Since patients' eligibility for Medicaid changes frequently, the amount paid by the State is only an approximate measure of total cost of care of the patient. To have one estimate of severity for a patient, the severity scores for each patient across all their episodes during the year were averaged. The averaged severity score ranged from 0.01 to 0.27. The mean was 0.03 (standard error=0.001).

Table 5 summarizes regression results. The dependent variable was "the amount paid by the State." All three independent variables—"the average severity of the episodes," "the number of episodes of the patient" and "the interaction between the severity and the number of episodes" —were statistically significant predictors of the dependent variable at alpha levels lower than 0.001. The R-Squared adjusted by degrees of freedom was 53%.

Data showed that episodes of care may be constructed from encounter databases. Furthermore, the proposed measure of episode of care explained a large percentage of variance in cost of care. The magnitude of the percent of variance explained by the measures reported here is of special interest. Many measures of severity and case mix report R2 values less than 10%. Because use of the present invention explains a large percent of the variance, confidence in the validity of the measure of severity of episodes is increased.

Table 1 is an example of a small database having a patient unique identification number, a diagnosis and a time of diagnosis.

TABLE 1

| Time (dd/mm/yy) | Patient ID | Diagnosis |
| --- | --- | --- |
| 01/01/01 | 1001 | A |
| 12/01/01 | 1001 | B |
| 22/01/01 | 1002 | A |
| 12/01/01 | 1002 | B |
| 22/01/01 | 1003 | C |
| 02/02/01 | 1001 | D |
| 02/02/01 | 1002 | B |
| 12/02/01 | 1003 | D |

TABLE 1-continued

| Time (dd/mm/yy) | Patient ID | Diagnosis |
| --- | --- | --- |
| 13/02/01 | 1003 | B |
| 01/05/01 | 1002 | C |

Create a query identifying for any pair of diagnoses the number of unique patients for whom the two diagnoses co-occur within 30 days. Note that the co-occurrence of diagnosis "a" and "b" does not depend on the order of which one comes first. Here is how the query may look like for the above example data:

TABLE 2

| First diagnosis | Second diagnosis | Co-occurrences |
| --- | --- | --- |
| A | A | 2 |
| A | B | 2 |
| A | C | 0 |
| A | D | 1 |
| B | A | 2 |
| B | B | 2 |
| B | C | 1 |
| B | D | 2 |
| C | A | 0 |
| C | B | 1 |
| C | C | 2 |
| C | D | 1 |
| D | A | 1 |
| D | B | 2 |
| D | C | 1 |
| D | D | 2 |

For each patient, the following analysis may be conducted. For the patient, when the same diagnosis occurs at two different time periods, rename the diagnoses into unique names—usually a combination of the name and date of diagnosis. For example patient 1002 has the following data when renamed:

TABLE 3

| Time (dd/mm/yy) | Patient ID | Diagnoses |
| --- | --- | --- |
| 12/01/01 | 1002 | B1201 |
| 22/01/01 | 1002 | A |
| 13/02/01 | 1002 | B1302 |
| 01/05/01 | 1002 | C |

For the patient, measure the absolute value of the length of time between any pair of diagnoses for the patient; refer to this as time between any two diagnoses. For example for patient 1002 the time between two different diagnoses may be:

TABLE 4

| First diagnosis | Second diagnosis | Time |
| --- | --- | --- |
| A | B1201 | 10 |
| A | B1302 | 21 |
| A | C | 38 |
| B1201 | A | 10 |
| B1201 | B1302 | 31 |
| B1201 | C | 48 |
| B1302 | A | 21 |
| B1302 | B1201 | 31 |
| B1302 | C | 17 |
| C | A | 38 |

TABLE 4-continued

| First diagnosis | Second diagnosis | Time |
| --- | --- | --- |
| C | B1201 | 48 |
| C | B1302 | 17 |

For the patient, look up the similarity of any pair of different diagnoses they have from step "2" and divide this by absolute value of the time between the two diagnoses, from step "b". this value may be referred to as the score. For example for the patient 1002 the results may be:

TABLE 5

| First diagnosis | Second diagnosis | Time |
| --- | --- | --- |
| A | B1201 | 2/10 = 0.20 |
| A | B1302 | 2/21 = .10 |
| A | C | 0/38 = 0 |
| B1201 | A | 2/10 = .20 |
| B1201 | B1302 | 2/31 = .06 |
| B1201 | C | 1/48 = 0.02 |
| B1302 | A | 2/21 = .10 |
| B1302 | B1201 | 2/31 = .06 |
| B1302 | C | 1/17 = .06 |
| C | A | 0/38 = 0 |
| C | B1201 | 1/48 = .02 |
| C | B1302 | 1/17 = .06 |

For the patient, standardized the score so that it ranges between 1 and zero by subtracting the minimum value from each score and dividing the results by the difference of maximum and minimum score. Refer to this as standardized score. For the patient 1002 the standardized score is as follows:

TABLE 6

| First | Second | Time |
| --- | --- | --- |
| A | B1201 | 1.0 |
| A | B1302 | .48 |
| A | C | .00 |
| B1201 | A | 1.0 |
| B1201 | B1302 | .32 |
| B1201 | C | .10 |
| B1302 | A | .50 |
| B1302 | B1201 | .30 |
| B1302 | C | .30 |
| C | A | .00 |
| C | B1201 | .10 |
| C | B1302 | .30 |

The different diagnoses may now be classified into episodes by using the standardized score. One classification procedure that could be used as per an embodiment of the present invention may include the following steps. Combine the two diagnoses with maximum standardized score into one episode if the value of the standardized score is higher than a pre-set cutoff—usually 0.5. Create a new diagnosis to represent the two diagnoses that were combined into an episode. Calculate the standardized score for this new diagnosis by averaging the standardized score of its two components. Exclude the diagnoses that have already been combined into new diagnoses from further analysis and repeat steps starting from step "i". For example, the data for case 1002 may follow these steps. Maximum is 1, therefore diagnoses A and B1201 may be combined.

TABLE 7

|       | A   | B1201 | B1302 | C   |
|-------|-----|-------|-------|-----|
| A     |     | 1.0   | .48   | .00 |
| B1201 | 1.0 |       | .32   | .10 |
| B1302 | .50 | .32   |       | .30 |
| C     | .00 | .10   | .30   |     |

A new diagnosis may now be created named AB1201 and standardized scores for the new diagnosis calculated as the average of its component.

TABLE 8

|       | A   | B1201 | AB1201        |
|-------|-----|-------|---------------|
| B1302 | .50 | .32   | (.5 + .32)/   |
| C     | .00 | .10   | (.00 + .10)   |

The diagnosis already combined into an episode may be excluded from further analysis and the steps repeated to find a new maximum of 0.41.

TABLE 9

|       | B1302 | C   | AB1201 |
|-------|-------|-----|--------|
| B1302 |       | .30 | .41    |
| C     | .30   |     | .05    |

The new maximum is not higher than the cutoff of 0.5. Therefore, no other diagnoses may be combined into new episodes. The result of the calculation for patient 1002 was three episodes. First, the combination of diagnosis A and diagnosis B on Jan. 12, 2001. Second, diagnosis B on Feb. 13, 2001 by itself. And third, diagnosis C by itself. Note that diagnosis B on Feb. 13, 2001 was not combined with diagnosis B on Jan. 12, 2001 even though both are the same diagnosis. Table 10 shows regression of "Amount paid by the State" on severity and number of episodes.

TABLE 10

Regression of "Amount paid by the State" on severity and number of episodes

|                                                          | Coefficients | P-value |
|----------------------------------------------------------|--------------|---------|
| Intercept                                                | −7297        | 0.003   |
| Average severity of episodes                             | −33.58       | 0.000   |
| Number of episodes                                       | 444971       | 0.000   |
| Product of number of episodes and average severity of episodes | 756          | 0.000   |
| Adjusted R Squared = 53.11%                              | Number of observations = 565 |         |

One may expect the performance of the approach disclosed herein may be different when parameters of the model are estimated from one database and applied to another unrelated database. Nevertheless, the magnitude of percent of variations in objective data explained by this approach is so high that even with changes in performance, this approach may remain relatively more accurate than many existing approaches.

The present invention may be used to construct episodes of care for specific diseases. Thus, if one investigator is interested in episodes for diabetes and another is interested in episodes of cancer, both may use the method disclosed here by pre-selecting patients with a particular disease.

A most appealing part of the present invention is the ease with which this approach may be integrated with existing databases. The presently disclosed model may work on any administrative database, which has information on date of visit and diagnosis. Any person familiar with database operations may implement it. In addition, electronic medical record companies may use the present invention to embed methods of analyzing performance of clinicians within their electronic record systems.

The foregoing descriptions of the preferred embodiments of the present invention have been presented for purposes of illustration and description. They are not intended to be exhaustive or to limit the invention to the precise forms disclosed, and obviously many modifications and variations are possible in light of the above teaching. The illustrated embodiments were chosen and described in order to best explain the principles of the invention and its practical application to thereby enable others skilled in the art to best utilize the invention in various embodiments and with various modifications as are suited to the particular use contemplated. For example, one skilled in the art will recognize that the present invention may used to track severity of episodes of care for various institutions. For example, a user of the present invention may examine episodes of care at institutions throughout the country to determine which institutions are showing success at treating particular diagnosis's. Similarly, the present invention may use other methods classifying the diagnoses based on the information desired. For example, an insurance company may perform the last classification process differently than a small private practice, and so, customize their classification process to meet their individual needs.

What is claimed is:

1. An episode classification system comprising:
 a. a multitude of diagnosis records, each of said diagnosis records including:
  i. diagnosis information;
  ii. time of said diagnosis information; and
  iii. patient information;
 b. a patient grouper for generating at least one patient group by grouping patient records having similar said patient information;
 c. a diagnosis grouper for generating at least one diagnosis group by grouping diagnosis records with similar said diagnosis information from said patient group;
 d. an episode analyzer including:
  i. a probability analyzer for performing probability calculations that are capable of generating a value that is proportional to a probability that shows whether at least two of said multitude of diagnosis records being used as input entries belong to a single episode, wherein said episode is a group of diagnoses on the same patient that describes the course of a given illness, and wherein a single probability calculation:
   a. operates on a pair of said diagnosis records;
   b. is a function of:
    i. a similarity value, said similarity value representing the similarity between said pair of said diagnosis records; and
    ii. a time between diagnosis value, said time between diagnosis value representing the time between said pair of said diagnosis records; and
   c. includes a probability numerator divided by a probability denominator, said probability numerator set to said similarity value times a first constant, and said probability denominator set to the quantity of a second constant times said time between diagnosis value plus one;

ii. an episode grouper for grouping said diagnosis records determined to belong to said single episode; and iii. a severity analyzer for performing episode severity calculations, said episode severity calculations capable of generating an episode severity value.

2. The episode classification system according to claim 1, wherein at least one of said diagnosis records is an anchor diagnosis record.

3. The episode classification system according to claim 1, wherein at least one of said diagnosis records is a trigger diagnosis record.

4. The episode classification system according to claim 1, wherein at least one of said diagnosis records is a stopping point diagnosis record.

* * * * *